United States Patent [19]

Blaudin de The et al.

[11] Patent Number: 5,223,606
[45] Date of Patent: Jun. 29, 1993

[54] STEROID/THYROID HORMONE RECEPTOR-RELATED PROTEIN INAPPROPRIATELY EXPRESSED IN HUMAN HEPATOCELLULAR CARCINOMA

[75] Inventors: Hughes Blaudin de The; Agnes Marchio; Pierre Tiollais; Anne DeJean, all of Paris, France

[73] Assignee: Institut Pasteur, Paris, France

[21] Appl. No.: 134,130

[22] Filed: Dec. 17, 1987

Related U.S. Application Data

[63] Continuation-in-part of Ser. No. 133,687, Dec. 16, 1987, abandoned.

[51] Int. Cl.$^5$ ............................................. C07K 13/00
[52] U.S. Cl. ..................................... 530/350; 530/828; 530/846; 435/69.1
[58] Field of Search .......................... 530/350, 828, 846

[56] References Cited

FOREIGN PATENT DOCUMENTS 0244221 11/1987 European Pat. Off. .

OTHER PUBLICATIONS

Petkovich, M. et al. "A Human Retinoic Acid Receptor . . . " Nature, vol. 330 pp. 444–450 Dec. 3, 1987.
Evans, R. "The Steroid and Thyroid Hormone Receptor Superfamily" Science vol. 240, pp. 889–895 May 13, 1988.
de Thé et al. "A Novel Steroid Thyroid Hormone Receptor-Related Gene . . . " Nature, vol. 330, pp. 667–670 Dec. 17, 1987.
Benbrook et al. "A New Retinoic Acid Receptor . . . " Nature 333, pp. 669–672 Jun. 16, 1988.
Brand, N. et al. "Identification of a Second Human Retinoic Acid Receptor" Nature v. 332 pp. 853–853, Apr. 28, 1988.
Dejean, A. et al. "Hepatitis B Virus DNA Integration . . . " Nature, vol. 322, pp. 70–72, Jul. 3, 1986.

Primary Examiner—Robert J. Hill, Jr.
Assistant Examiner—Nina Ossanna
Attorney, Agent, or Firm—Finnegan, Henderson, Farabow, Garrett & Dunner

[57] ABSTRACT

A previously isolated hepatitis B virus (HBV) integration in a 147 bp cellular DNA fragment linked to hepatocellular carcinoma (HCC) was used as a probe to clone the corresponding complementary DNA from a human liver cDNA library. Nucleotide sequence analysis revealed that the overall structure of the cellular gene, which has been named hap, is similar to that of the DNA-binding hormone receptors. Six out of seven hepatoma and hepatoma-derived cell-lines express a 2.5 kb hap mRNA species which is undetectable in normal adult and fetal livers, but present in all non-hepatic tissues analyzed. Low stringency hybridization experiments revealed the existence of hap related genes in the human genome. The cloned DNA sequence is useful in the preparation of pure hap protein and as a probe in the detection and isolation of complementary DNA and RNA sequences.

5 Claims, 6 Drawing Sheets

```
CGGGGTAGGATCCGGAACGCATTCGGAAGGCTTTTTGCAAGCATTTACTTGGAAGGAGAACTTGGGATCTTTCTG      75

GGAACCCCCCGCCCCGGCTGGATTGGCCGAGCAAGCCTGGAAAATGGTAAATGATCATTTCCATCAATTACAGGC    150

TTTTAGCTGGCTTGTCTGTCATAATTCATGATTCGGGGCTGGGAAAAAGACCAACAGCCTACGTGCCAAAAAAGG   225

GGCAGAGTTTGATGGAGTTGGGTGGACTTTTCTATGCCATTTGCCTCCACACCTAGAGGATAAGCACTTTTGCAC   300
                                   1           10
                                    MetPheAspCysMetAspValLeuSerValSerProGlyGlnIleLeuAspPhe
ACATTCAGTGCAAGGGAGATCATGTTTGACTGTATGGATGTTCTGTCAGTGAGTCCTGGGCAAATCCTGGATTTC   375
          20                  30                  40
TyrThrAlaSerProSerSerCysMetLeuGlnGluLysAlaLeuLysAlaCysPheSerGlyLeuThrGlnThr
TACACTGCGAGTCCGTCTTCCTGCATGCTCCAGGAGAAAGCTCTCAAAGCATGCTTCAGTGGATTGACCCAAACC   450
                    50                  60
GluTrpGlnHisArgHisThrAlaGlnSerIleGluThrGlnSerThrSerSerGluGluLeuValProSerPro
GAATGGCAGCATCGGCACACTGCTCAATCAATTGAAACACAGAGCACCAGCTCTGAGGAACTCGTCCCAAGCCCC   525
          70                  80 ──▶             90
ProSerProLeuProProProArgValTyrLysProCysPheValCysGlnAspLysSerSerGlyTyrHisTyr
CCATCTCCACTTCCTCCCCCTCGAGTGTACAAACCCTGCTTCGTCTGCCAGGACAAATCATCAGGGTACCACTAT   600
                  100                 110
GlyValSerAlaCysGluGlyCysLysGlyPhePheArgArgSerIleGlnLysAsnMetIleTyrThrCysHis
GGGGTCAGCGCCTGTGAGGGATGTAAGGGCTTTTTCCGCAGAAGTATTCAGAAGAATATGATTTACACTTGTCAC   675
          120                 130                 140
ArgAspLysAsnCysValIleAsnLysValThrArgAsnArgCysGlnTyrCysArgLeuGlnLysCysPheGlu
CCAGATAAGAACTGTGTTATTAATAAAGTCACCAGGAATCGATGCCAATACTGTCGACTCCAGAAGTGCTTTGAA   750
         ◀──           150                 160
ValGlyMetSerLysGluSerValArgAsnAspArgAsnLysLysLysGluThrSerLysGlnGluCysThr
GTGGGAATGTCCAAAGAATCTGTCAGGAATGACAGGAACAAGAAAAAGAAGGAGACTTCGAAGCAAGAATGCACA   825
          170                 180                 190
GluSerTyrGluMetThrAlaGluLeuAspAspLeuThrGluLysIleArgLysAlaHisGlnGluThrPhePro
GAGAGCTATGAAATGACAGCTGAGTTGGACGATCTCACAGAGAAGATCCGAAAAGCTCACCAGGAAACTTTCCCT   900
                   200                 210
SerLeuCysGlnLeuGlyLysTyrThrThrAsnSerSerAlaAspHisArgValArgLeuAspLeuGlyLeuTrp
TCACTCTGCCAGCTGGCTAAATACACCACGAATTCCAGTGCTGACCATCGAGTCCGACTGGACCTGGGCCTCTGG   975
          220                 230                 240
AspLysPheSerGluLeuAlaThrLysCysIleIleLysIleValGluPheAlaLysArgLeuProGlyPheThr
GACAAATTCAGTGAACTGGCCACCAAGTGCATTATTAAGATCGTGGAGTTTGCTAAACGTCTGCCTGGTTTCACT  1050
                  250                 260
GlyLeuThrIleAlaAspGlnIleThrLeuLeuLysAlaAlaCysLeuAspIleLeuIleLeuArgIleCysThr
GGCTTGACCATCGCAGACCAAATTACCCTGCTGAAGGCCGCCTGCCTGGACATCCTGATTCTTAGAATTTGCACC  1125
          270                 280                 290
ArgTyrThrProGluGlnAspThrMetThrPheSerAspGlyLeuThrLeuAsnArgThrGlnMetHisAsnAla
AGGTATACCCCAGAACAAGACACCATGACTTTCTCAGACGGCCTTACCCTAAATCGAACTCAGATGCACAATGCT  1200
                   300                 310
GlyPheGlyProLeuThrAspLeuValPheThrPheAlaAsnGlnLeuLeuProLeuGluMetAspAspThrGlu
GGATTTGGTCCTCTGACTGACCTTGTGTTCACCTTTGCCAACCAGCTCCTGCCTTTGGAAATGGATGACACAGAA  1275
          320                 330                 340
ThrGlyLeuLeuSerAlaIleCysLeuIleCysGlyAspArgGlnAspLeuGluGluProThrLysValAspLys
ACAGGCCTTCTCAGTGCCATCTGCTTAATCTGTGGAGACCGCCAGGACCTTGAGGAACCGACAAAAGTAGATAAG  1350
                  350                 360
LeuGlnGluProLeuLeuGluAlaLeuLysIleTyrIleArgLysArgArgProSerLysProHisMetPhePro
CTACAAGAACCATTGCTGGAAGGACTAAAAATTTATATCAGAAAAAGACGACCCAGCAAGCCTCACATGTTTCCA  1425
          370                 380                 390
LysIleLeuMetLysIleThrAspLeuArgSerIleSerAlaLysGlyAlaGluArgValIleThrLeuLysMet
AAGATCTTAATGAAAATCACAGATCTCCGTAGCATCAGTGCTAAAGGTGCAGAGCGTGTAATTACCTTGAAAATG  1500
```

FIG. 2A

```
                    400                          410
GluIleProGlySerMetProProLeuIleGlnGluMetMetGluAsnSerGluGlyHisGluProLeuThrPro
GAAATTCCTGGATCAATGCCACCTCTCATTCAAGAAATGATGGAGAATTCTGAAGGACATGAACCCTTGACCCCA 1575
        420                          430                       440
SerSerSerGlyAsnThrAlaGluHisSerProSerIleSerProSerSerValGluAsnSerGlyValSerGln
AGTTCAAGTGGGAACACAGCAGAGCACAGTCCTAGCATCTCACCCAGCTCAGTGGAAAACAGTGGGGTCAGTCAG 1650

SerProLeuValGlnSTOP
TCACCACTCGTGCAATAAGACATTTTCTAGCTACTTCAAACATTCCCCAGTACCTTCAGTTCCAGGATTTAAAAT 1725
GCAAGAAAAAACATTTTTACTGCTGCTTAGTTTTTGGACTGAAAAGATATTAAAACTCAAGAAGGACCAAGAAGT 1800
TTTCATATCTATCAATATATATACTCCTCACTGTGTAACTTACCTAGAAATACAAACTTTTCCAATTTTAAAAAA 1875
TCAGCCATTTCATGCAACCAGAAACTAGTTAAAAGCTTCTATTTTCCTCTTTGAACACTCAAGATGCATGGCAAA 1950
GACCCAGTCAAAATGATTTACCCCTGGTTAAGTTTCTGAAGACTTTGTACATACAGAAGTATGGCTCTGTTCTTT 2025
CTATACTGTATGTTGGTGCTTTCCTTTTGTCTTGCATACTCAAAATAACCATGACACCAAGGTTATGAAATAGA 2100
CTACTGTACACGTCTACCTAGGTTCAAAAAGATAACTGTCTTGCTTTCATGGAATAGTCAAGACATCAAGGTAAG 2175
GAAACAGGACTATTGACAGGACTATTGTACAGTATGACAAGATAAGGCTGAAGATATTCTACTTTAGTTAGTATG 2250
GAAGCTTGTCTTTGCTCTTTCTGATGCTCTCAAACTGCATCTTTTATTTCATGTTGCCCAGTAAAAGTATACAAA 2325
TTCCCTGCACTAGCAGAAGAGAATTCTGTATCAGTGTAACTGCCAGTTCAGTTAATCAAATGTCATTTGTTCAAT 2400
TGTTAATGTCACTTTAAATTAAAAGTGGTTTATTACTTGTTTAATGACATAACTACACAGTTAGTTAAAAAAAAT 2475
TTTTTTACAGTAATGATAGCCTCCAAGGCAGAAACACTTTTCAGTGTTAAGTTTTTGTTTACTTGTTCACAAGCC 2550
ATTAGGGAAATTTCATGGGATAATTAGCAGGCTGGTCTACCACTGGACCATGTAACTCTAGTGTCCTTCCTGATT 2625
CATGCCTGATATTGGGATTTTTTCCAGCCCTTCTTGATGCCAAGGGCTAATTATATTACATCCCAAAGAAACAG 2700
GCATAGAATCTGCCTCCTTTGACCTTGTTCAATCACTATGAAGCAGAGTGAAAGCTGTGGTAGAGTGGTTAACAG 2775
ATACAACTGTCAGTTTCTTAGTTCTCATTTAAGCACTAGTGGAATTTTTTTTTTGATATATTAGCAAGTCTGTG 2850
ATGTACTTTCACTGGCTCTGTTTGTACATTGAGATTGTTTGTTTAACAATGCTTTCTATGTTCATATACTGTTTA 2925
CCTTTTTCCATGGAGTCTCCTGGCAAAG AATAAA TATATTTATTTTAAAAAAAAAAAAAAAAAAAA      2992
```

FIG. 2B

| | | | $M_r$ (K) |
|a|b|c| |
| | | |— 97|
| | | |— 68|
| | | |— 43|
| | | |— 26|

FIG. 6

STEROID/THYROID HORMONE RECEPTOR-RELATED PROTEIN INAPPROPRIATELY EXPRESSED IN HUMAN HEPATOCELLULAR CARCINOMA

This application is a continuation-in-part of application U.S. Ser. No. 07/133,687, filed Dec. 16, 1987, now abandoned.

BACKGROUND OF THE INVENTION

Primary hepatocellular carcinoma (HCC) represents the most common cancer, especially in young men, in many parts of the world (as in China and in much of Asia and Africa) (reviewed in Tiollais et al., 1985). Its etiology was investigated mostly by epidemiological studies, which revealed that, beyond some minor potential agents such as aflatoxin and sex steriod hormones, hepatitis B virus (HBV) chronic infection could account for a large fraction of liver cancers (Beasley and Hwang, 1984).

HBV DNA has been found to be integrated in the genome of most cases of HCCs studied (Edman et. al., 1980; Brechot et al., 1980; Chakraborty et al., 1980; Chen et al., 1982). Nonetheless the role of those sequences in liver oncogenesis remains unclear.

A single HBV integration in a HCC sample in a short liver cell sequence has been reported recently. The sequence was found to be homologous to steroid receptor genes and to the cellular proto-oncogene c-erbA (Dejean et al., 1986).

Ligand-dependent transcriptional activators, such as steroid or thyroid hormone receptors, have recently been cloned allowing rapid progress in the understanding of their mechanism of action. Nevertheless, there exists a need in the art for the identification of transcripts that may encode for activitational elements, such as nuclear surface receptors, that may play a role in hepatocellular carcinoma. Such findings would aid in identifying corresponding transcripts in susceptible individuals. In addition, identification of transcripts could aid in elucidating the mechanisms by which HCC occurs.

SUMMARY OF THE INVENTION

This invention aids in fulfilling these needs in the art. More particularly, this invention provides a cloned DNA sequence encoding for a polypeptide of a newly identified cellular gene, which has been named hap. The DNA sequence has the formula shown in FIGS. 2A and 2B. The invention also covers variants of the DNA sequence. The DNA sequence is in a purified form.

This invention also provides a probe consisting of a radionuclide bonded to the DNA sequence of the invention.

In addition, this invention provides a hybrid duplex molecule consisting essentially of the DNA sequence of the invention hydrogen bonded to a nucleotide sequence of complementary base sequence, such as DNA or RNA.

Further, this invention provides a polypeptide comprising an amino acid sequence of hap protein, wherein the polypepetide contains the amino acid sequence shown in FIGS. 2A and 2B and serotypic variants thereof. The polypeptide is free from human serum proteins, virus, viral proteins, human tissue and human tissue components. Preferably, the polypeptide is free from human, blood-derived protein.

Also, this invention provides a process for selecting a nucleotide sequence coding for hap protein or a portion thereof from a group of nucleotide sequences comprising the step of determining which of the nucleotide sequences hybridizes to a DNA sequence of the invention. The nucleotide sequence can be a DNA sequence or a RNA sequence. The process can include the step of detecting a label on the nucleotide sequence.

Still further, this invention provides a recombinant vector comprising lambda-NM1149 having an EcoRI restriction endonuclease site into which has been inserted the DNA sequence of the invention. The invention also provides plasmid pCOD20, which comprises the DNA sequence of the invention.

Finally, this invention provides an *E. coli* bacterial culture in a purified form, wherein the culture comprises *E. coli* cells containing DNA, wherein a portion of the DNA comprises the DNA sequence of the invention. Preferably, the *E. coli* is stain TG-1.

BRIEF DESCRIPTION OF THE DRAWINGS

This invention will be described in greater detail with reference to the drawings in which

FIGS. 2A and 2B are the nucleotide sequence of human liver hap cDNA and a predicted amino acid sequence of human liver hap cDNA;

FIG. 6 shows the alignment of hap translated amino acid sequence with several known sequences for thyroid and steroid hormone receptors;

DetAILED DESCRIPTION OF PREFERRED EMBODIMENTS

As previously noted, ligand-dependent transcriptional activators, such as steroid or thyroid hormone receptors, have recently been cloned. The primary structure and expression of a new gene, hap, closely related to steroid or thyroid hormone receptor genes have now been discovered. The hap product exhibits two regions highly homologous to the conserved DNA- and hormone-binding domains of previously cloned receptors.

More particularly, the cloning of a cDNA corresponding to a novel steroid/thyroid hormone receptor-related gene has been achieved. The cDNA was recovered from a human liver cDNA library using a labelled cellular DNA fragment previously isolated from a liver tumor. The fragment contained a 147 bp putative exon in which HBV inserted. The sequence of this cellular gene, which is referred to herein as hap for hepatoma, reveals various structural features characteristic of c-erbA/steroid receptors (Dejean et al., 1986). The receptor-related protein is likely to be a novel member of the superfamily of transcriptional regulatory proteins that includes the thyroid and steroid hormone receptors.

It has been discovered that the hap gene is transcribed at low level in most human tissues, but the gene is overexpressed in prostate and kidney. Moreover, six out of seven hepatoma and hepatoma-derived cell lines express a small hap transcript, which is undetectable in normal adult and fetal livers, but is present in all non-hepatic tissues tested. Altered expression of hap may be involved in liver oncogenesis.

These findings, as well as other discoveries relating to this invention, will now be described in detail.

A human liver cDNA library was screened using a nicktranslated 350 bp EcoRI genomic fragment (MNT probe) previously cloned from a hepatoma sample. The fragment contained the putative 147 bp cellular exon in which HBV integration took place (Dejean et al., 1986).

Four positive 3' co-terminal clones were isolated from the $2.10^6$ plaques screened and the restriction maps were deduced for each of the cDNA clone EcoRI inserts. The longest one was identified lambda-13. The restriction map of lambda-13 is shown in FIG. 1.

Figure 1:
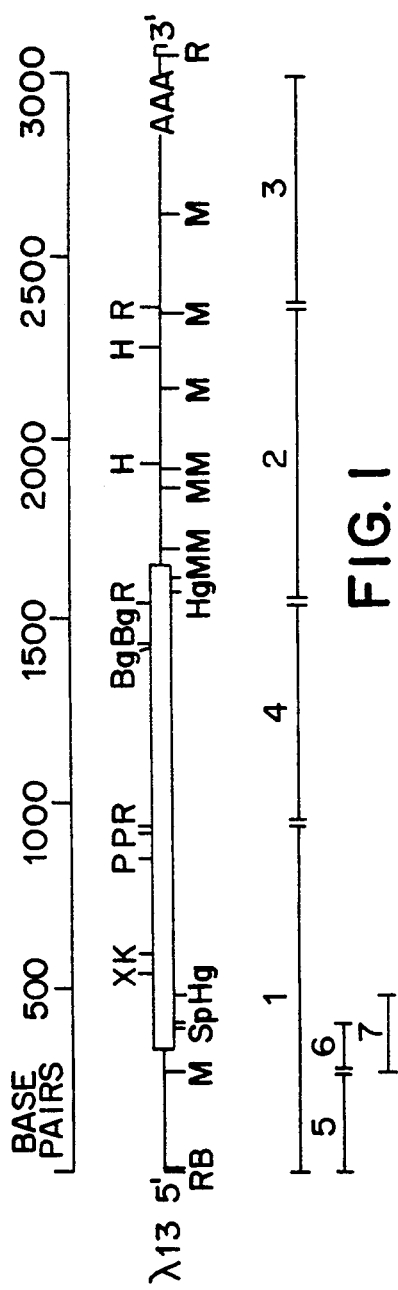
FIG. 1 is a restriction map of human liver hap cDNA.

Referring to FIG. 1, the insert of clone lambda-13 is nearly a full-length cDNA for the hap gene. Noncoding sequences (lines) and coding sequences (boxed portion) are indicated. Restriction sites are:

R EcoRI
Bg BglII
M MaeI
X XhoI
K KDnI
P PvuII
B BamHI
H HindIII.

The lambda-13 clone was subjected to nucleotide sequence analysis. The nucleotide sequence is shown in FIGS. 2A and 2B. The nucleotide sequence of the hap cDNA is presented in the 5' to 3' orientation. The numbers on the right refer to the position of the nucleotides. Numbers above the deduced translated sequence indicate amino acid residues. The four short open reading frames in the 5' untranslated region are underlined. Adenosine residues (20) are found at the 3' end of lambda-13. The putative polyadenylation signal site (AATAAA) is boxed. The region homologous to the DNA-binding domain of known thyroid/steroid hormone receptors is indicated by horizontal arrows. The exon, previously cloned from a HCC sample genomic DNA library and in which HBV integration took place, is bracketed.

This invention of course includes variants of the nucleotide sequence shown in FIGS. 2A and 2B encoding hap protein or a serotypic variant of hap protein exhibiting the same immunological reactivity as hap protein.

The DNA sequence of the invention is in a purified form. Generally, the DNA sequence is free of human serum proteins, viral proteins, and nucleotide sequences encoding these proteins. The DNA sequence of the invention can also be free of human tissue.

The DNA sequence of the invention can be used as probe for the detection of a nucleotide sequence in a biological material, such as tissue or body fluids. The polynucleotide probe can be labeled with an atom or inorganic radical, most commonly using a radionuclide, but also perhaps with a heavy metal.

In some situations it is feasible to employ an antibody which will bind specifically to the probe hybridized to a single stranded DNA or RNA. In this instance, the antibody can be labeled to allow for detection. The same types of labels which are used for the probe can also be bound to the antibody in accordance with known techniques.

Conveniently, a radioactive label can be employed. Radioactive labels include $^{32}P$, $^{3}H$, $^{14}C$, or the like. Any radioactive label can be employed, which provides for an adequate signal and has sufficient half-life. Other labels include ligands, that can serve as a specific binding member to a labeled antibody, fluorescers, chemiluminescers, enzymes, antibodies which can serve as a specific binding pair member for a labeled ligand, and the like. The choice of the label will be governed by the effect of the label on the rate of hybridization and binding of the probe to the DNA or RNA. It will be necessary that the label provide sufficient sensitivity to detect the amount of DNA or RNA available for hybridization.

Ligands and anti-ligands can be varied widely. Where a ligand has a natural receptor, namely ligands such as biotin, thyroxine, and cortisol, these ligands can be used in conjunction with labeled naturally occurring receptors. Alternatively, any compound can be used, either haptenic or antigenic, in combinations with an antibody.

Enzymes of interest as labels are hydrolases, particularly esterases and glycosidases, or oxidoreductases, particularly peroxidases. Fluorescent compounds include fluorescein and its derivatives, rhodamine and its derivatives, dansyl, umbelliferone, etc. Chemiluminescers include luciferin and luminol.

Amino Acid Sequence of Protein Encoded by hap Gene

Based upon the sequence of the hap cDNA, the amino acid sequence of the protein encoded by hap gene was determined. With reference to FIGS. 2A and 2B, the deduced amino acid sequence encoded by the gene reveals a long open reading frame of 448 amino acids corresponding to a predicted polypeptide of relative molecular mass 51,000.

A putative initiator methionine codon and an in-frame terminator codon are positioned respectively at nucleotides 322 and 1666 in the sequence (FIGS. 2A and 2B). However, two other methionine codons are found 4 and 26 triplets downstream from the first ATG making the determination of the initiation site equivocal.

The coding sequence is preceded by a 5' region of at least 321 nucleotides which contains four short open reading frames delineated by initiator and stop codons (FIGS. 2A and 2B). Translation usually starts, in eukaryotes, at the 5' most ATG triplet, but the finding of open reading frames in the 5' 'untranslated' region is not unprecedented (Kozak, 1986). It is not known yet whether those sequences are used for translation and exert any function in the cell.

In the 3' untranslated region, 1326 nucleotides long, no long open reading frame is present. A putative polyadenylation signal (AATAAA) is found 19 bp upstream from the polyadenylation site.

It will be understood that the present invention is intended to encompass the protein encoded by the hap gene, i.e. hap protein, and fragments thereof in highly purified form. The hap protein can be expressed in a suitable host containing the DNA sequence of the invention. This invention also includes polypeptides in which all or a portion of the binding site of hap protein is linked to a larger carrier molecule, such as a polypeptide or a protein, and in which the resulting product exhibits specific binding in vivo and in vitro. In this case, the polypeptide can be smaller or larger than the proteinaceous binding site of the protein of the invention.

It will be understood that the polypeptide of the invention encompasses molecules having equivalent peptide sequences. By this it is meant that peptide sequences need not be identical. Variations can be attributable to local mutations involving one or more amino acids not substantially affecting the binding capacity of the polypeptide. Variations can also be attributable to structural modifications that do not substantially affect binding capacity. Thus, for examples, this invention is intended to cover serotypic variants of hap protein.

Three particular regions of hap gene are of interest. Two of them are located in the D region (amino acids comprised between No. 146 and No. 196) which are shown by the inventors to be highly immunogenic.

Peptides corresponding to amino acids comprised between No. 151 and No. 167 are synthesized by Merrifiel techniques. They are injected in mice and monoclonal and polyclonal antibodies are obtained. Classical methods are used for the preparation of the hybridomas. The antibodies are used to quantify the amount of human receptors produced by patients in order to correlate the pathological states of the illness and quantity or absence of receptors.

The second peptide in the D region is located between amino acids No. 175 and No. 185.

The third peptide is located at the end of E region between amino acids 440 and 448.

Other peptides having formulas derived from the nucleotidic sequence of hap gene, could be used as reagents particularly to obtain antibodies for diagnostic purposes as defined hereinabove.

Depending on the use to be made of the proteins of the invention, it may be desirable to label the proteins. Examples of suitable labels are radioactive labels, enzymatic labels, flourescent labels, chemiluminescent labels, or chromophores. The methods for labeling proteins of the invention do not differ in essence from those widely used for labeling immunoglobulin.

Tissue Specific mRNA Distribution

In order to study expression of the hap gene, Northern blot analysis was performed using MNT as a probe and poly(A)+RNA extracted from various human tissues and cell lines. The results are shown in FIG. 3.

More particularly, Northern blot analyses were performed with poly(A)+RNAs (15 μg per lane) extracted from different human organs and cell lines. A control hybridization with a mouse beta-actin cDNA probe is shown below the hybridizations in FIG. 3. Hap mRNA in different tissues is shown in FIG. 4A as follows:

Lane a ovary
Lane b uterus
Lane c HBL 100 mammary cells
Lane d adult spleen
Lane e 18 weeks fetal spleen
Lane f K562
Lane g HL60 hematopoeitic cell lines
Lane h prostatic adenoma
Lane l kidney
Lane j adult liver
Lane k 18 weeks fetal liver.
Lanes a–k correspond to a one day exposure.

Figure 3:
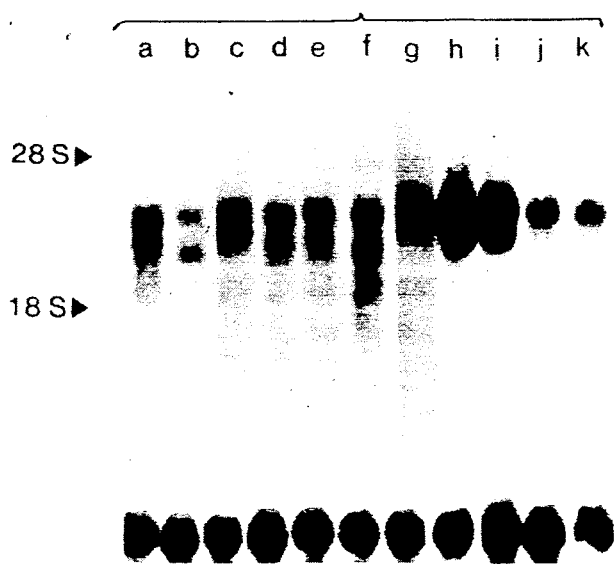
FIG. 3 depicts the distribution of hap mRNA in different tissues as determined by Northern blot analysis.

FIG. 3 shows that two RNA species of 3 kb and +2.5 kb (the size of this smaller mRNA is slightly variable from one organ to another) were expressed at low abundance in ovary (lane a), uterus (lane b), HBL 100 mammary cells (lane c), adult and fetal spleen (lane d and e, respectively), and K562 and HL60 hematopoeitic cell lines (lanes f and g, respectively). Surprisingly, an approximately tenfold higher level of expression was detected in prostatic adenoma (lane h) and kidney (lane i). By contrast, a single mRNA of 3000 nucleotides, expressed at low levels, was present in poly(A) RNA from adult and fetal liver tissues (lanes j and k). Therefore, the cloned hap cDNA is likely to be a full-length copy of this transcript.

The finding of two mRNA species overexpressed in prostate and kidney, as well as the presence of a single mRNA expressed at low level in adult and fetal livers show that hap expression is differentially regulated in those organs. This tissue specific expression provides some indication that prostate and kidney, as well as liver, could be key tissues and that hap functions in those cell types may differ.

Figure 4:
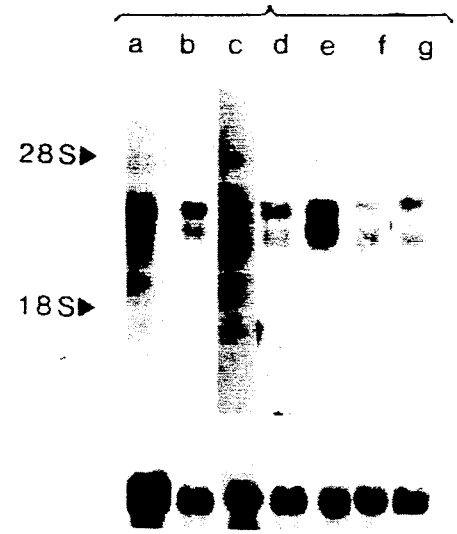
FIG. 4 depicts the distribution of hap mRNA in HCC and HCC derived cell lines as determined by Northern blot analysis.

FIG. 4 shows hap mRNA in HCC and HCC derived cell-lines as follows:

Lane a, normal liver (four days autoradiography);
Lanes b, c, d: three HCC samples (Lane b, patient Ca; Lane c, patient Mo; Lane d, patient TCl);
Lanes e, f, g: three HCC-derived cell lines (Lane e, PLC/PRF/5; Lane f, HEPG2; Lane g, HEP 3B). The lanes b-g correspond to a one day exposure. Once again, a control hybridization with a normal beta-actin cDNA probe is shown below the hybridizations.

With reference to FIG. 4, the smaller 2.5 kb mRNA was undetectable, even after long exposure, in three adult and two fetal human livers analyzed (FIG. 4, Lane a). This differential expression in normal livers may suggest a distinct role of hap in this particular tissue.

Northern blot analysis of human HCCs and hepatoma cell lines showed almost constant alterations in hap transcription. There are two possible alternatives to explain this result. The smaller mRNA species can be simply expressed as a consequence of the cellular dedifferentiation. The tumorous liver cell, having lost its differentiated characteristics, would behave as any other cell type and thus express the same 2.5 kb mRNA as found in non-hepatic cells. However, the inability to detect such a smaller transcript in fetal livers does not seem to favor this hypothesis. On the contrary, the presence of the smaller transcript may have preceded the tumorigenesis events and would rather reflect a preneoplastic state. The presence of an inappropriately expressed hap protein, normally absent from normal hepatocytes, may have directly participated to the hepatocellular transformation. In this respect, the previous study reporting a HBV integration in the hap gene of a human HCC (Dejean et al., 1986) strongly supports the idea that hap could be causatively involved in liver oncogenesis. Indeed, in this tumor, a chimeric gene between the viral pre-S1 gene and hap may have resulted in the over-expression of a truncated hap protein. At present, it is the one found in non-hepatic tissues.

Expression of hap in Hepatocellular Carcinoma

Hap was first identified in a human primary liver cancer. Encouraged by this finding, poly(A)+RNA from seven hepatoma and hepatoma-derived cell lines were analyzed by Northern-blotting. Five of them contained integrated HBV DNA sequences. In addition to the 3 kb long mRNA found in normal adult and fetal liver, an additional +2.5 kb RNA species was observed, in equal or even greater amount, in three out of four HCC (FIG. 4, Lanes b, c, d) and in the PLC/PRF/5, HEPG2 and HEP3B hepatoma cell-lines (Lanes e, f, g). The size of the smaller transcript was variable from sample to sample. In addition, the two transcripts were strikingly overexpressed, at least ten fold, in the PLC/PRF/5 cells.

To test the possibility that the inappropriate expression of hap in those six tumors and tumorous cell-lines might be the consequence of a genomic DNA alteration, Southern-blotting of cellular DNA was performed using, as two probes, the MNT fragment together with a 1 kb EcoRI fragment corresponding to the 5' extremity of the cDNA insert (FIGS. 2A and 2B). No rearrangement and/or amplification was detected with any of these two probes which detect a different single exon (data not shown), suggesting that the hap gene was not altered at the genomic level. It is yet unknown whether the +2.5 kb mRNA, present in the liver tumorous samples and cell lines, corresponds to the same smaller transcript as that found in non-hepatic tissues. However, its presence in the liver seems to be clearly associated to the hepatocellular transformed state.

Hormone-binding Assay

Amino-acid homologies between the hap protein and the c-erbA/steroid receptors support the hypothesis that hap may be a receptor for a thyroid/steroid hormone-related ligand. The ability to express functional receptors in vitro from cloned c-erbA/steroid receptor genes led to the use of an in vitro translation assay to identify a putative hap ligand.

Figure 5:
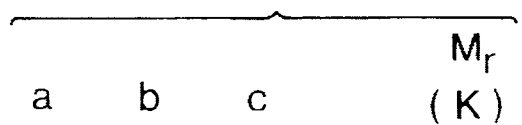
FIG. 5 is a fluorograph of hap polypeptide synthesized in vitro and isolated on SDS-polyacrylamide gel.

The coding region of hap was cloned into pTZ18 plasmid vector to allow in vitro transcription with the T7 RNA polymerase and subsequent translation in reticulocyte lysates. The results are shown in FIG. 5. More particularly, $^{35}$S-methionine-labelled products synthesized using T7 polymerase-catalysed RNA transcripts were separated on a 12% SDS-polyacrylamide gel, which was fluorographed (DMSO-PPO). The lanes in FIG. 5 are as follows:

Lane a, pCOD 20 (sense RNA, 70 ng)
Lane b, pCOD 20 (140 ng)
Lane c, pCOD 14 (antisense RNA, 140 ng).

FIG. 5 shows that the hap RNA directed the efficient synthesis of a major protein, with a 51 K relative molecular mass, consistent with the size predicted by the amino acid sequence (lanes a and b), whereas the antisense RNA-programmed lysate gave negligible incorporation (lane c).

Because c-erbA and hap colocalize on chromosome 3 and are more closely related according to their amino acid sequence, ($^{125}$I)-T3 (triiodothyronine), -reverse T3 (3,3',5'-triiodothyronine) and -T4 (thyroxine), were first tested for their binding with the in vitro translated hap polypeptide. No specific fixation with any of those three thyroid hormones could be detected. As a positive control, binding of a T3 was detected with nuclear extracts from HeLa cells. The results were negative as well when the experiment was repeated with (3H) -retinol, -retinoic acid, and -testosterone, which represent three putative ligands for hap whose receptors have not yet been cloned. Although it cannot be excluded that hap may encode a hormone independent transcriptional activator, it is more likely that hap product, i.e. the hap protein, is a receptor for a presently unidentified hormone.

Similarity of HAP Protein to Thyroid/Steroid Hormone Receptors

The c-erbA gene product, recently identified as a receptor for thyroid hormone (Weinberger, et al., 1986; Sap et al., 1986), as well as the steroid receptors, belong to a superfamily of regulatory proteins, which consequently to their binding with specific ligand, appear capable of activating the transcription of target genes (reviewed by Yamamoto, 1985). This activation seems to be the result of a specific binding of the hormone-receptor complex to high-affinity sites on chromatin.

Comparative sequence analysis has been made between the following different cloned steroid receptors:

glucocorticoid receptor (GR) (Hollenberg et Al., 1985; Miesfeld et al., 1986);

oestrogen receptor (ER) (Green et al., 1986; Greene et al., 1986);

progesterone receptor (PR) (Conneely et al., 1986; Loosfelt et al., 1986); and thyroid hormone receptor (c-erbA product) (Weinberger et al., 1986; Sap et al. 1986).

Mutation analysis has also been carried out. (Kumar et al., 1986; Hollenberg et al., 1987; Miesfeld et al., 1987). The results revealed the presence of two conserved regions representing the putative DNA-binding and hormone-binding domains of those molecules. It has now been discovered that hap protein is homologous to the thyroid/steroid hormone receptors.

Figure 6:
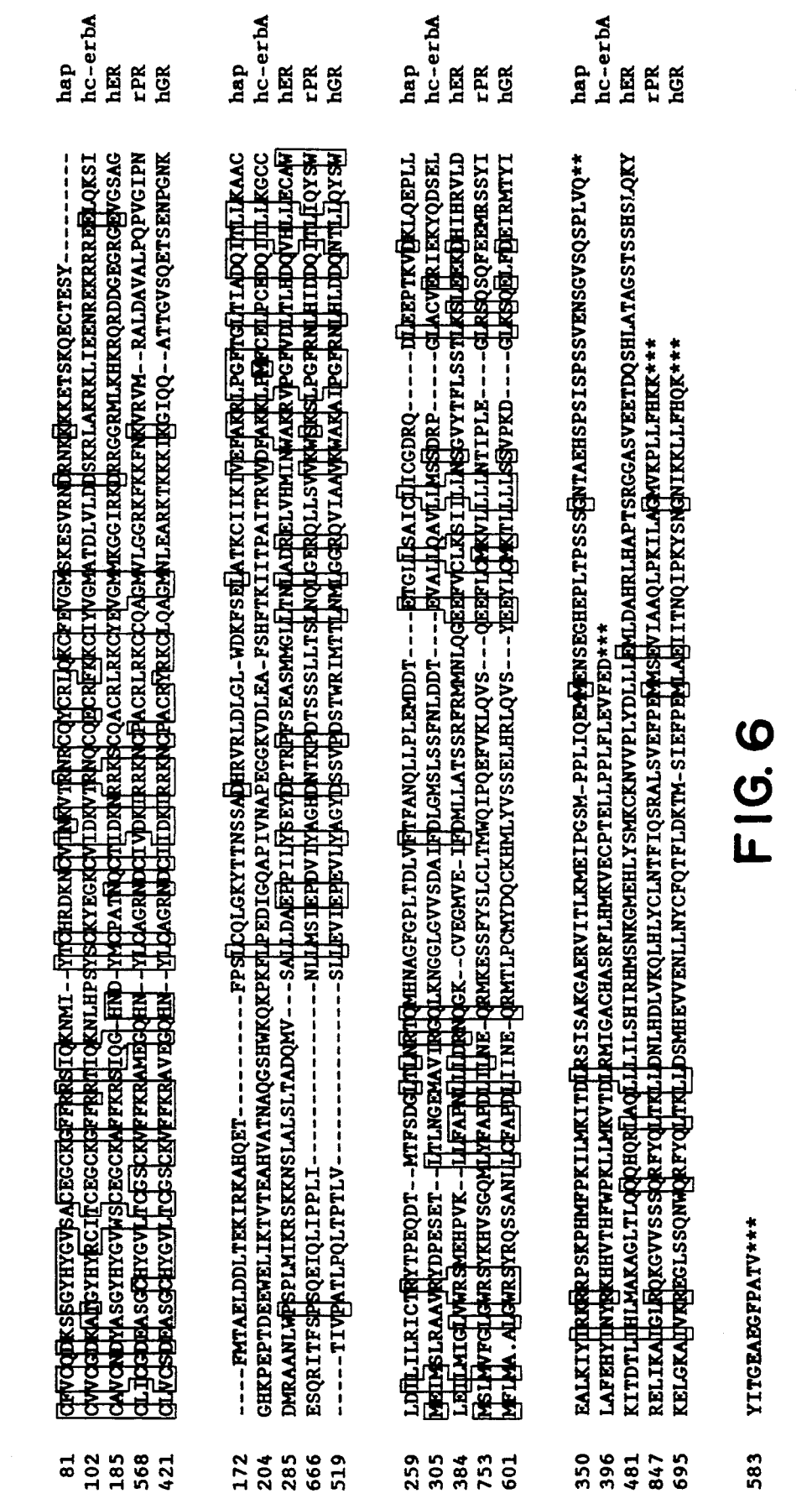

More particularly, homology previously reported between the putative 147 bp cellular exon (bracketed in FIGS. 2A and 2B) and the c-erbA/steroid receptor genes led us to compare the entire hap predicted amino acid sequence with hGR, rPR, hER and hc-erbA/- thyroid hormone receptor. The five sequences have been aligned for maximal homology by the introduction of gaps. The results are depicted in FIG. 6. Specifically, the following nucleotide sequences were aligned after a computer alignment of pairs (Wilbur and Lipman, 1983):

hap product, human placenta c-erbA protein (hc-erbA, Weinberger et al., 1986), human oestrogen receptor (hER, Green et al., 1986), rabbit progesterone receptor (rPR, Loosfelt et al., 1986), and human glucocorticoid receptor (hGR, Hollenberg et al., 1985).

A minimal number of gaps (-) was introduced in the alignment. Amino acid residues matched in at least three of the polypeptides are boxed. The one letter code for amino acids is:

A Ala
C Cys
D Asp
E Glu
F Phe
G Gly
H His
I Ile
K L Leu
M Met
N Asn
P Pro
Q Gln
R Arg
S Ser
T Thr

V Val
Y Tyr

The sequence comparison analysis revealed that the two regions highly conserved in the thyroid/steroid hormone receptors are similarly conserved in the hap product. Consequently, the overall organization of hap is much similar to that of the four receptors in that it can be roughly divided into four regions (arbitrarily referred to as A/B, C, D and E (Krust et al., 1986)).

In C, the most highly conserved region, extending from amino-acid 81 to 146 in hap, the nine cysteines already conserved between the four known receptors are strikingly present at the same positions. Comparison between the cysteine-rich region of with the corresponding region of the four receptors reveals 64% amino acid identity with hc-erbA, 59% with hER, 42% with rPR and 44% with hGR. This is schematically represented in FIG. 7.

Figure 7:
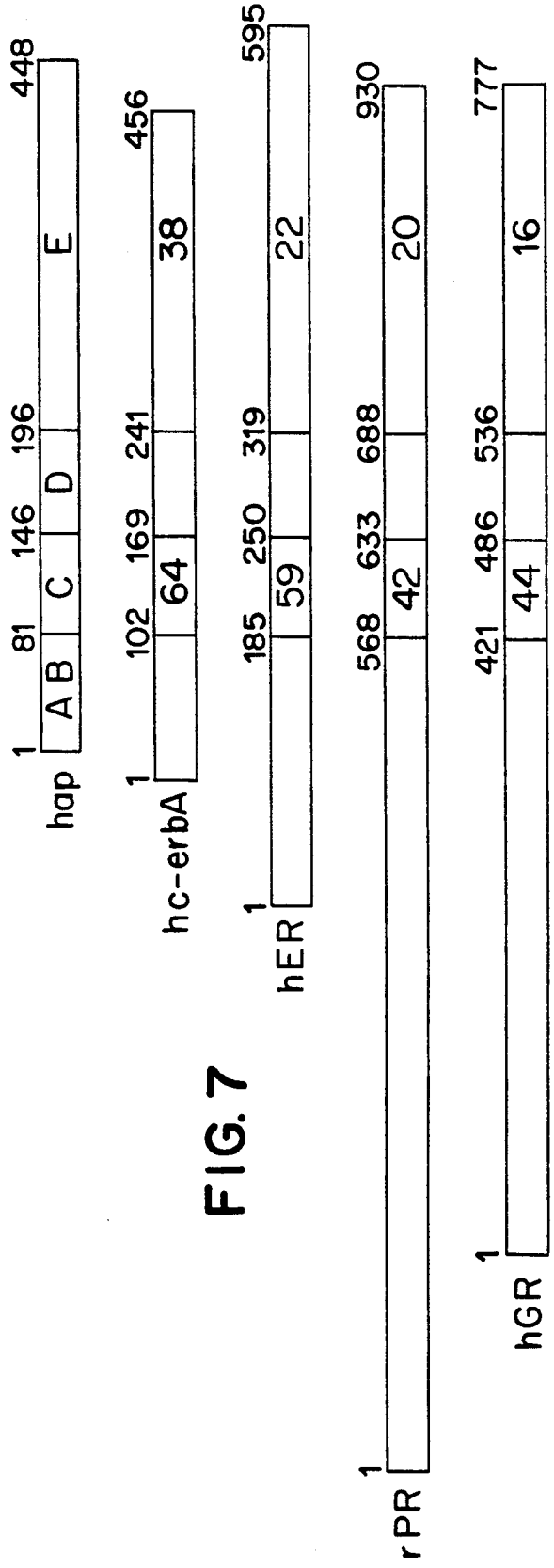
FIG. 7 is a schematic alignment of similar regions identified as A/B, C, D, and E of the amino acid sequences of FIG. 6.

Referring to FIG. 7, a schematic alignment of the five proteins can be seen. The division of the thyroid/steroid hormone receptor regions A/B, C, D, E is schematically represented in the hap protein. The two highly conserved regions, identified as the putative DNA-binding (region C) and hormone-binding (region E) domains of the receptors, are shown as stippled blocks. The numbers refer to the position of amino acid residues. The sequences of each of the hc-erbA product, hER, rPR and hGR receptors are compared with the hap protein. The numbers present in the stippled blocks correspond to the percentage of homology between hap protein on the one hand and each of the receptors on the other hand in the two highly conserved regions C and E. The empty blocks correspond to the non-conserved A/B and D regions.

It has also been found that hap shares 47% homology in the C region with the chicken vitamin D3 receptor (VDR), recently cloned as a partial cDNA (McDonnel et al., 1987) (data not shown). Apart from c-erbA, which contains two additional residues, the 66 amino acid long C region shows a constant length in hER, VDR, hGR, rPR and hap sequences.

Region E (residue 195-448), which is well-conserved, but to a lesser extent, shows a slightly stronger homology to hc-erbA (38%) (FIG. 7). The hap/hc-erbA homology, however, remains inferior to the identity found between hGR and rPR (90 and 51 percent in regions C and E, respectively). No significant homology was observed when comparing the A/B (residue 1-80) and D (147-194) regions which are similarly variable, both in sequence and length, in the four known receptors.

It is thus evident from FIGS. 6 and 7 that the hap product exhibits two highly homologous regions. The C domain is characterized by strikingly conserved Cys-X2-Cys units, evoking those found in the DNA-binding transcriptional factor TFIIIA (Miller et al., 1985) and in some protein that regulated development, such as Kruppel (Rosenberg et al., 1986). In the latter, the Cys-X2-Cys, together with His-X3-His units, can form metal binding fingers that are crucial for DNA-binding (Berg, 1986; Diakun et al., 1986). Similarly, the C domain of previously cloned receptors are likely to contain metal binding fingers and were shown to bind DNA (Hollenberg et al., 1987; Miesfeld et al., 1987). Since the C region of the hap gene product shares 24/66 conserved amino acids with all all steroid or thyroid hormone receptors, including all nine cysteine residues, it is likely that the hap protein is a DNA-binding protein. Hap, as c-erbA/steroid receptors, may modulate the transcription of target genes.

In addition, the significant homology detected in the E domain suggests that hap product is a ligand-binding protein and directs the question of the nature of the putative ligand. Hap protein seems to differ too much from previously cloned hormone receptors to be a variant of one of them. In addition, the in vitro translated 51 K hap polypeptide failed to bind all ligand tested. Although that hap gene product could be a ligand-independent DNA-binding protein, it is believed that hap encodes a receptor for a presently unidentified circulating or intracellular ligand.

It has been proposed that steroid and thyroid hormone receptor genes were derived from a common ancestor (Green and Chambon, 1986). This primordial gene may have provided to the receptors their common scaffolding while the hormone and target gene cellular DNA specificities were acquired through mutations accumulated in the C and E domains. Hap is both linked to the steroid receptor gene by its shorter C domain (66AA) and to the thyroid hormone receptor genes by its clearly greater homology with c-erbA in the E region (38%). This suggests that hap ligand may belong to a different hormone family.

Different functions have been assigned to the four regions defined in the glucocorticoid and oestrogen receptors (Kumar et al, 1986; Giguere et al., 1986; Miesfeld et al., 1987). By analogy, the regions C and E may represent, respectively, the putative DNA-binding and hormone-binding domains of the hap protein. The precise functions of the A/B and D domains remain unknown. The presence of the amino-terminal A/B region of the human GR has been recently shown to be necessary for full transcriptional activity (Hollenberg et al., 1987), whereas results obtained with the rat GR indicated it was dispensable (Miesfeld et al., 1987). From this alignment study it appears that hap is distinct, but closely related to the thyroid/steroid hormone receptor genes suggesting that its product may be a novel ligand-dependent, DNA-binding protein.

Hap related genes

Figure 8A:
FIG. 8 depicts hap related genes in vertebrates (A) and in humans and (B and C) as determined by Southern blot analysis.

Southern blotting was performed on restriction enzyme-digested DNAs obtained from different organisms with labelled genomic MNT fragment containing the first exon of the cysteine-rich region of hap. The results are shown in FIG. 8. More particularly, hap related genes in vertebrates (A) and in humans (B and C) were compared. Cellular DNA (20 μg) from various sources was digested with BqlII and subjected to Southern blot analysis using the MNT probe under non-stringent hybridization and washing conditions. The lanes in FIG. 8A are identified as follows:
Lane a human liver
Lane b domestic dog liver
Lane c woodchuck (marmota monax)
Lane d mouse liver (BALB/c strain)
Lane e chicken erythrocytes
Lane f cartilaginous fish (Torpedo).

As illustrated in FIG. 8A, BqlII fragments that anneal effectively with MNT probe under non-stringent hybridization and washing conditions are present in digests of DNA from several mammals (mouse, woodchuck, dog) as well as from bird and fish. If this blotting experiment is performed at high stringency, no hybridization is observed with heterologous DNA (data not shown). These data suggest that the hybridizing sequences represent evolutionarily conserved homologs of hap.

Figure 8B:
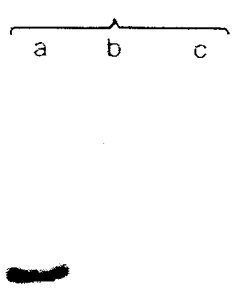

The existence of multiple c-erbA and GR genes (Jansson et al., 1983; Weinberger et al., 1986; Hollenberg et al., 1985) encouraged a search for hap related genes in the human genome. Thus, human liver DNA digested by PstI, BamHI, and EcoRI was analyzed by Southern blot, using the MNT probe, under stringent conditions. The results are shown in FIG. 8B. After digestion of liver DNA by PstI (lane a), BamHI (lane b), or EcoRI (lane c), a single band is observed with the MNT probe in high stringency hybridization.

Figure 8C:
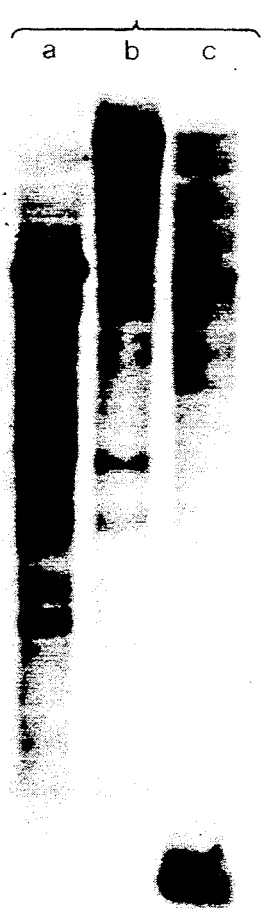

The same blot was hybridized with the MNT probe under nonstringent hybridization and washing conditions. The results are shown in FIG. 8C. When Southern blotting was performed under relaxed hybridization conditions, additional bands were observed in the products of each enzyme digestion (FIG. 8C, lanes a, b, c). For example, seven faint hybridizing fragments of 1, 1.7, 2.4, 3.8, 5.5, 6, 7.4 kb were observed in the BamHI digestion (lane b). None of those bands cross-hybridized with a human c-erbA probe (data not shown). A minimum of three faint bands in the PstI lane suggests the existence of at least four related hap genes in the human genome.

From a panel of somatic cell hybrids, hap was assigned to chromosome 3 (Dejean, et al., 1986). To find out whether the hap related genes were all chromosomally linked or not, DNAs from human liver LA.56U and 53K cell-lines (two mouse/human somatic cell hybrids containing, altogether, most human chromosomes except chromosome 3 (Nguyen Van Cong et al., 1986)), and mouse lymphoid cells were BamHI digested, transferred to nitrocellulose, and hybridized to the MNT probe in low-stringency conditions. Of the seven faint bands present in the human liver DNA track, two at least were conserved in the LA.56U and/or L.53K cell lines DNAs digestion (data not shown) indicating that some of the hap genes do not localize on chromosome 3. Altogether the results suggest that hap belongs to a multigene family consisting of at least four members dispersed in the human genome.

The experimental procedures used in carrying out this invention will now be described in greater detail.

EXPERIMENTAL PROCEDURES cDNA Cloning and Screening

Briefly, the cDNA was synthesized using oligo dT primed poly-A+ liver mRNA, using the method of Gubler and Hoffman (1983) (C. de Taisne, unpublished data). cDNA's were size selected on a sucrose gradient and the fraction corresponding to a mean size of 3 kb was treated with EcoRI methylase. After addition of EcoRI linkers, the cDNA was digested by EcoRI and ligated to an EcoRI restricted lambda-NM1149. After in vitro encapsidation, the phages were amplified on C600 hfl and $2.10^6$ recombinant were plated at a density of 10,000 per dish. The dishes were transfered to nylon filters and hybridized to the 350 bp EcoRI-EcoRI genomic fragment (MNT) previously described (Dejean et al., 1986). Four positive clones were isolated and the restriction map of each insert was determined. The longest one, clone lambda-13, was subjected to nucleotide sequence analysis.

Nucleotide Sequence

Clone lambda-13 DNA was sonicated, treated with the Klenow fragment of DNA polymerase plus deoxyribonucleotides (2 hr., 15° C.) and fractionated by agarose gel electrophoresis. Fragments of 400-700 bp were excised and electroeluted. DNA was ethanol-precipitated, ligated to dephosphorylated SmaI cleaved M13 mp8 replication form DNA and transfected into Excherichia coli strain TG-1 by the high-efficiency technique of Hanahan (1983). Recombinant clones were detected by plaque hybridization using either of the four EcoRI fragments of cDNA insert as probes (FIG. 1). Single-stranded templates were prepared from plaques exhibiting positive hybridization signals and were sequenced by the dideoxy chain termination procedure (Sanger et al., 1977) using buffer gradient gels (Biggin et al., 1983).

Northern Blots

Cytoplasmic RNA was isolated from the fresh tissue using guanidine thiocyanate, and the RNA cell line was extracted using isotonic buffer and 0.5% SDS, 10 mn Na acetate pH 5.2. RNAs were then treated with hot phenol. Poly(A)+RNA (15 μg) of the different samples were separated on a 1% agarose gel containing glyoxal, transfered to nylon filters and probed using the nick-translated MNT fragment. The experimental procedure is described in Maniatis et al. (1982).

Southern Blot

20 μg of genomic DNA was digested to completion, fractionated on a 0.8% agarose gel and transfered to nylon paper. Low stringency hybridization was performed as follows: 24 hr prehybridization in 35% formamide, 5× Denhardt, 5× SSC, 300 μg/ml denatured salmon sperm DNA, at 40° C.; 48 hr hybridization with 35% formamide, 5× Denhardt, 5× SSC, 10% Dextran sulfate, $2.10^6$ cpm/ml denatured $^{32}P$ labelled DNA probe (specific activity $5 \times 10^8$ cpm/μg). Washes were made in 2× SSC, 0.1 SDS, 55° C. for 15 min. High stringency hybridization conditions were the same except that 50% formamide was used with 24 hr hybridization. Washing was in 0.1× SSC, 0.1 SDS, 55° C. for 30 min.

Construction of Plasmids for In-Vitro Translation

The 3 kb insert of phage lambda-13 was excised from the phage DNA by partial EcoRI digestion, electroeluted and digested by BamHI and HindIII. To remove most of the untranslated sequences, the 1.8 kb cDNA fragment obtained was then partially digested by MaeI (Boehringer). The 1.4 kb MaeI-MaeI fragment, extending from the first to the third MaeI site in the cDNA insert sequence (FIG. 1) and containing the complete coding region was mixed with SmaI cut dephosphorylated pTZ18 (Pharmacia), the extremities were filled in using Kleenow fragment of DNA PolI (Amersham) and ligated. Two plasmids were derived: pCOD20 (sense) and pCOD14 (antisense).

Translation and hormone binding assays pCOD20 and pCOD14 were linearized with HindIII. Capped mRNA was generated using 5 μg of DNA, 5 μM rNTP, 25 mM DTT, 100 U RNAsin (Promega), 50 U T7 Pol (Genofit) in 40 mM Tris pH 8, 8 mM MgCl₂, 2 mM spermidine, 50 mM NaCl, in 100 μl at 37° C. Capping was performed by omitting GTP and adding CAP ($m^7$ G (5') ppp (5') G) (Pharmacia) for the 15 first minutes of the reaction. Translation was performed using rabbit reticulocyte lysate (Amersham) under the suggested conditions using 40 µl of lystae for 2.5 µg of capped RNA.

The thyroid hormone binding assays included 5 µl of lysate in (0.25M sucrose, 0.25 KCl, 20 mM Tris (pH 7.5), 1 mM MgCl$_2$, 2 mM EDTA, 5 mM DTT) with 1 mM [$^{125}$I] T4, [$^{125}$I] T3 or [$^{125}$I] rT3 (specific activity: T4, rT3 1400 mCi/mg Amersham, T3 3000 mCi/mg NEN). After at least 2 hr of incubation at 0° C., free was separated from bound by filtration through millipore HAWP 02500 filters using 10 ml of ice cold buffer. For testosterone, retinol, retinoic acid 10 µl of lysate were added to 45 lambda of 20 mM Tris pH 7.3, 1 mM EDTA, 50 mM NaCl, 2 mM beta-mercaptoethanol and 5 mM testosterone, 400 mM retinol or 15 mM retinoic acid (81 Ci/mmol; 60 Ci/mmol; 46 Ci/mmol; Amersham). After an overnight incubation at 0° C. free was separated from bound by Dextran coated charcoal (0.5% Norit A–0.05% T70) and centrifugation. All experiments were performed in duplicates and parallel experiments were performed with 100 fold excess corresponding cold hormone.

In summary, a hepatitis B virus (HBV) integration in a 147 bp cellular DNA fragment homologous to steroid receptors and c-erbA/thyroid hormone receptor genes previously isolated from a human hepatocellular carcinoma (HCC) was used as a probe to clone the corresponding complementary DNA from a human liver cDNA library. The nucleotide sequence analysis revealed that the overall structure of the cellular gene, named hap is similar to that of DNA-binding hormone receptors. That is, it displays two highly conserved regions identified as the putative DNA-binding and hormone-binding domains of the c-erbA/steroid receptors. Six out of seven hepatoma and hepatoma-derived cell-lines express a 2.5 kb hap mRNA species which is undetectable in normal adult and fetal livers but present in all non-hepatic tissues analyzed. Low stringency hybridization experiments revealed the existence of hap related genes in the human genome. Taken together, the data suggest that the hap product may be a member of a new family of ligand-responsive regulatory proteins whose inappropriate expression in liver seems to correlate with the hepatocellular transformed state.

Because the known receptors control the expression of target genes that are crucial for cellular growth and differentiation, an altered receptor could participate in the cell transformation. In that sense, avian v-erbA oncogene, which does not by itself induce neoplasms in animals, potentiates the erythroblast transformant effects of v-erbB and other oncogenes of the src family (Kahn et al., 1986). It has been shown that the v-erbA protein has lost its hormone-binding potential (Sap et al., 1986), presumably as a result of one or several mutations it has accumulated in its putative ligand-binding domain. It has been also suggested (Edwards et al., 1979) that the growth of human breast tumors are correlated to the presence of significant levels of ER. This invention may provide a novel example in which a DNA-binding protein would again relate to the oncogenic transformation by interfering with the transcriptional regulation of target genes. DNA-transfection assays using the native hap cDNA as well as 'altered' hap genes derived from various HCC can provide important information concerning any transforming capacity.

Following is a more detailed identification of the literature citations appearing above in parentheses:

Beasley, R. P., and Hwang, L. Y. (1984). Epidemiology of Hepatocellular Carcinoma In Viral Hepatitis and Liver Disease, G. N. Vyas, J. L. Dienstag, J. H. Hoofnagle, eds, (Grune and Stratton, Inc.), pp. 209–224.

Berg, J. M. (1986). More metal-binding fingers. Nature, 319, 264–265.

Biggin, M. D., Gibson, T. J. and Hong, G. F. (1983. Buffer gradient gels and $^{35}$S label as an aid to rapid DNA sequence determination. Proc. Natl. Acad. Sci. USA, 80, 3963–3965.

Bréchot, C., Pourcel, C., Louise, A., Rain, B. and Tiollais, P. (1980). Presence of integrated hepatitis B virus DNA sequences in cellular DNA of human hepatocellular carcinoma. Nature, 286, 533–535.

Chakraborty, P. R., Ruiz-Opazo, N., Shouval, D. and Shafritz, D. A. (1980). Nature, 286, 531–533.

Chen, D. S., Hoyer, B. H., Nelson, J., Purcell, R. H. and Gerin, J. L. (1982). Detection and properties of hepatitis B viral DNA in liver tissues from patients with hepatocellular carcinoma. Hepatology, 2, 42S–45S.

Conneely, O. M., Sullivan, W. P., Toft, D. O., Birnbaumer, M., Cook, R. G., Maxwell, B. L., Zarucid-Schulz, T., Greene, G. L., Schrader, W. T. and O'-Malley, B. W. (1986). Molecular cloning of the chicken progesterone receptor. Science, 233, 767–770.

Degean, A., Bougueleret, L., Grzeschik, K. H. and Tiollais, P. (1986). Hepatitis B virus DNA integration in a sequence homologous to v-erbA and steroid receptor genes in a hepatocellular carcinoma. Nature, 322, 70–72.

Diakun, G. P., Fairall, L. and Klug, A. (1986). EXAFS study of the zinc-binding sites in the protein transcription factor IIIA. Nature, 324, 698–699.

McDonnell D. P., Mangelsdorf, D. J., Pike, J. W., Haussler, M. R. and O'Malley, B. W. (1987). Molecular cloning of complementary DNA encoding the avian receptor for vitamin D. Science, 235, 1214–1217.

Edman, J. C., Gray, P., Valenzuela, P., Rall, L. B. and Rutter, W. J. (1980). Integration of hepatitis B virus sequences and their expression in a human hepatoma cell. Nature, 286, 535–538.

Edwards, D. P., Chamness, G. C., McGuire, W. L. (1979). Estrogen and progesterone receptor proteins in breast cancer. Biochimica et Biophysica Acta, 560, 457–486.

Giguere, V., Hollenberg, S. M., Rosenfeld, M. G. and Evans, R. M. (1986). Functional Domains of the human glucocorticoid receptor. Cell, 46, 645–652.

Green, S., Walter, P., Kumar, V., Krust, A., Bornert, J. M., Argos, P. and Chambon, P. (1986). Human oestrogen receptor cDNA: sequence, expression and homology to v-erb-A. Nature, 320, 134–139.

Green, S. and Chambon, P. (1986). A superfamily of potentially oncogenic hormone receptors. Nature, 324, 615–617.

Greene, G. L., Gilna, P., Waterfield, M., Baker, A., Hort, Y. and Shine, J. (1986). Sequence and expression of human estrogen receptor complementary DNA, Science, 231, 1150–1154.

Gubler, U. and Hoffman, B. J. (1983). A simple and very efficient method for generating cDNA libraries. Gene, 25, 263–269.

Hanahan, D. (1983). Studies on transformation of Escherichia coli with plasmids. J. Mol. Biol. 166, 557–580.

Hollenberg, S. M., Weinberger, C., Ong., E. S., Cerelli, G., Oro, A., Lebo, R., Thompson, E. G., Rosenfeld, M. G. and Evans, R. M. (1985). Primary structure and expression of a functional human glucocorticoid receptor. Cell, 49, 39–46.

Jansson, M., Philipson, L. and Vennstrom, B. (1983). Isolation and characterization of mulltiple human genes homologous to the oncogenes of avian erythroblastosis virus. The EMBO J., 2, 561–565.

Kahn, P., Frykberg, L., Brady, C., Stanley, I., Beug, H., Vennstrom, B. and Graf, T. (1986). v-erbA cooperates with sarcoma oncogenes in leukemic cell transformation. Cell, 45, 349–356.

Kozak, M., (1986). Bifunctional messenger RNAs in eukaryotes. Cell, 47, 481–483.

Krust, A., Green,, S., Argos, P., Kumar, V., Walter, P., Bornert, J. M. and Chambon, P. (1986). The chicken oestrogen receptor sequence: homology with v-erbA and the human oestrogen and glucocorticoid receptors. The EMBO J., 5, 891–897.

Kumar, V., Green, S., Staub, A. and Chambon, P. (1986). Localisation of the oestradiol-binding and putative DNA-binding domains of the human oestrogen receptor. The EMBO J., 5, 2231–2236.

Loosfelt H., Atger, M., Misrahi, M., Guiochon-Mantel, A., Meriel, C., Logeat, F., Bernarous, R. and Milgrom, E. (1986). Cloning and sequence analysis of rabbit progesterone-receptor complementary DNA. Proc. Natl. Acad. Sci USA, 83, 9045–9049.

Maniatis, T., Fritch, E. and Sambrook, J. (1982). Molecular cloning: a laboratory manual (Cold Spring Harbor, New-York: Cold Spring Harbor Laboratory).

Miesfeld, R., Rusconi, S., Godowski, P. J., Maler, B. A., Okret, S., Wilkstrom, A. C., Gustafsson, J. A. and Yamamoto, K. R. (1986). Genetic complementation of a glucocorticoid receptor deficiency by expression of cloned receptor cDNA. Cell, 46, 389–399.

Miesfeld R , Godowski, P. J., Maler, B. A. and Yamamoto, K. R. (1987. Glucocorticoid receptor mutants that define a small region sufficient for enhancer activation. Science, 236, 423–427.

Miller, J., McLachlan, A. D. and Klug, A. (1985). Repetitive zinc-binding domains in the protein transcription factor IIIA from Xenopus oocytes. The EMBO J., 4, 1609–1614.

Nguyen Van Cong, Weil, D., Finaz, C., Cohen-Haguenauer, O., Gross, M. S., Jegou-Foubert, C., de Tand, M. F., Cochet, C., de Grouchy, J., Frezal, J. (1986). Panel of twenty-five independent man-rodent hybrids for human genetic marker mapping Ann. Genet., 29, 20–26.

Rosenberg, U. G., Schroder, C., Preiss, A., Kienlin,, A., Coté, S., Riede, I. and Jackle, H. (1986). Structural homology of the product of the Drosophila Kruppel gene with Xenopus transcription factor IIIA. Nature, 319, 336–339.

Sanger, F., Nicklen,, S. and Coulson, A. R. (1977). DNA sequencing with chain-terminating inhibitors. Proc. Natl. Acad. Sci. USA, 74, 5463–5467.

Sap, J., Munoz, A., Damm, K., Goldberg, Y., Ghysdael, J., Leutz, A., Beug, H. and Vennstrom, B. (1986). The c-erb-A protein is a high affinity receptor for thyroid hormone. Nature, 324, 635–640.

Szmuness, W. (1973). Hepatocellular carcinoma and the hepatitis B virus evidence for a causal association. Prog. Med. Virol., 24, 40–69.

Tiollais, P., Pourcel, C. and Dejean, A. (1985). The hepatitis B virus Nature, 317, 489–495.

Weinberger, C., Thompson, C. C., Ong, E. S., Lebo, R., Gruol, D. J. and Evans, R. M. (1986). The c-erb-A gene encodes a thyroid hormone receptor. Nature, 324, 641–646.

Wilbur, W. J. and Lipman, D. J. (1983). Rapid similarity searches of nucleic acid and protein data banks. Proc. Natl. Acad. Sci. USA, 80, 726–730.

Yamamoto, K. R. (1985). Steroid receptor regulated transcription of specific genes and gene networks. Ann. Rev. Genet., 19, 209–252.

What is claimed is:

1. An isolated or synthetic polypeptide consisting essentially of an amino acid sequence, wherein said amino acid sequence is:

```
1                                    10
HetPheAspCysMetAspValLeuSerValSerProGlyGlnIleLeuAspPhe 20                            30
TyrThrAlaSerProSerSerCysHetLeuGlnGluLysAlaLeuLysAlaCys 40                          50
PheSerGlyLeuThrGlnThrGluTrpGlnHisArgHisThrAlaGlnSerIle

60
GluThrGlnSerThrSer Ser Glu Glu Leu Val Pro Ser Pro
                   GCTCTGAGGAACTCGTCCCAAGCCCC
    70                              80
ProSerProLeuProProProArgValTyrLysProCysPheValCysGlnAsp 90                         100
LysSerSerGlyTyrHisTyrGlyValSerAlaCysGluGlyCysLysGlyPhe 110                  120
PheArgArgSerIleGlnLysAsnMetIleTyrThrCysHisArgAspLysAsn 130                        140
CysValIleAsnLysValThrArgAsnArgCysGlnTyrCysArgLeuGlnLys

150
CysPheGluValGlyHetSerLysGluSerValArgAsnAspArgAsnLysLys 160                             170
LysLysGluThrSerLysGlnGluCysThrGluSerTyrGluMetThrAlaGlu 180                    190
LeuAspAspLeuThrGluLysIleArgLysAlaHisGlnGluThrPheProSer 200                    210
LeuCysGlnLeuGlyLysTyrThrThrAsnSerSerAlaAspHisArgValArg 220                    230
LeuAspLeuGlyLeuTrpAspLysPheSerGluLeuAlaThrLysCysIleIle

240
LysIleValGluPheAlaLysArgLeuProGlyPheThrGlyLeuThrIleAla 250                    260
AspGlnIleThrLeuLeuLysAlaAlaCysLeuAspIleLeuIleLeuArgIle 270                    280
CysThrArgTyrThrProGluGlnAspThrHetThrPheSerAspGlyLeu 290                        300
ThrLeuAsnArgThrGlnMetHisAsnAlaGlyPheGlyProLeuThrAsp

310
LeuValPheThrPheAlaAsnGlnLeuLeuProLeuGluHetAspAspThr 320                    330
GluThrGlyLeuLeuSerAlaIleCysLeuIleCysGlyAspArgGlnAspLeu 340                        350
GluGluProThrLysValAspLysLeuGlnGluProLeuLeuGluAlaLeu 360                        370
LysIleTyrIleArgLysArgArgProSerLysProHisMetPheProLysIle
```

-continued

380
LeuMetLysIleThrAspLeuArgSerIleSerAlaLysGlyAlaGluArgVal 390                                    480
IleThrLeuLysHetGluIleProGlySerMetProProLeuIleGlnGluHet 410                                    420
HetGluAsnSerGluGlyHisGluProLeuThrProSerSerGlyAsnThr 430                                    440
AlaGluHisSerProSerIleSerProSerSerValGluAsnSerGlyValSer

450
GlnSerProLeuValGln.

2. An isolated or synthetic polypeptide as claimed in claim 1, wherein said polypeptide is free from human serum proteins, virus, viral protein, human tissue, and human tissue components.

3. An isolated or synthetic polypeptide as claimed in claim 1, wherein said polypeptide is free from human blood derived protein.

4. A polypeptide of hap protein, wherein the polypeptide consists essentially of the amino acid sequence:

MetPheAspCysMetAspValLeuSerValSerProGlyGlnIleLeuAspPheTyrThrAla
SerProSerSerCysMetLeuGlnGluLysAlaLeuLysAlaCysPheSerGlyLeuThrGln
ThrGluTrpGlnHisArgHisThrAlaGlnSerIleGluThrGlnSerThrSerSerGluGlu
LeuValProSerProProSerProLeuProProProArgValTyrLysProCysPheValCys
GlnAspLysSerSerGlyTyrHisTyrGlyValSerAlaCysGluGlyCysLysGlyPhePhe
ArgArgSerIleGlnLysAsnMetIleTyrThrCysHisArgAspLysAsnCysValIleAsn
LysValThrArgAsnArgCysGlnTyrCysArgLeuGlnLysCysPheGluValGlyMetSer
LysGluSerValArgAsnAspArgAsnLysLysLysLysGluThrSerLysGlnGluCysThr
GluSerTyrGluMetThrAlaGluLeuAspAspLeuThrGluLysIleArgLysAlaHisGln
GluThrPheProSerLeuCysGlnLeuGlyLysTyrThrThrAsnSerSerAlaAspHisArg
ValArgLeuAspLeuGlyLeuTrpAspLysPheSerGluLeuAlaThrLysCysIleIleLys
IleValGluPheAlaLysArgLeuProGlyPheThrGlyLeuThrIleAlaAspGlnIleThr
LeuLeuLysAlaAlaCysLeuAspIleLeuIleLeuArgIleCysThrArgTyrThrProGlu
GlnAspThrMetThrPheSerAspGlyLeuThrLeuAsnArgThrGlnMetHisAsnAlaGly
PheGlyProLeuThrAspLeuValPheThrPheAlaAsnGlnLeuLeuProLeuGluMetAsp
AspThrGluThrGlyLeuLeuSerAlaIleCysLeuIleCysGlyAspArgGlnAspLeuGlu
GluProThrLysValAspLysLeuGlnGluProLeuLeuGluAlaLeuLysIleTyrIleArg
LysArgArgProSerLysProHisMetPheProLysIleLeuMetLysIleThrAspLeuArg
SerIleSerAlaLysGlyAlaGluArgValIleThrLeuLysMetGluIleProGlySerMet
ProProLeuIleGlnGluMetMetGluAsnSerGluGlyHisGluProLeuThrProSerSer
SerGlyAsnThrAlaGluHisSerProSerIleSerProSerSerValGluAsnSerGlyVal
SerGlnSerProLeuValGln, linked to a carrier molecule, wherein said polypeptide is free from human serum proteins, virus, viral protein, human tissue, and human tissue components.

5. The polypeptide as claimed in claim 4, which is free from human, blood-derived protein.

* * * * *

UNITED STATES PATENT AND TRADEMARK OFFICE
CERTIFICATE OF CORRECTION

PATENT NO. : 5,223,606
DATED : June 29, 1993
INVENTOR(S) : Hugues Blaudin de The et al.

It is certified that error appears in the above-indentified patent and that said Letters Patent is hereby corrected as shown below:

Claim 1, column 16, line 18, change "Het" to --Met--;
line 21, change "Het" to --Met--;
line 39, change "Het" to --Met--;
line 56, change "Het" to --Met--; and
line 61, change "Het" to --Met--.

Claim 1, column 17, line 6, change "Het" to --Met-- (both occurrences); and
line 9, change "Het" to --Met--.

Signed and Sealed this

Twenty-second Day of August, 1995

Attest:

BRUCE LEHMAN

*Attesting Officer*   *Commissioner of Patents and Trademarks*